(12) United States Patent
Vielhaber et al.

(10) Patent No.: US 8,278,068 B2
(45) Date of Patent: Oct. 2, 2012

(54) EX VIVO HUMAN SKIN MODEL

(75) Inventors: Gabriele Vielhaber, Holzminden (DE); Paolo Pertile, San Pietro Viminario (IT)

(73) Assignees: Symrise AG, Holzminden (DE); Cutech SRL, Padua (IT)

( * ) Notice: Subject to any disclaimer, the term of this patent is extended or adjusted under 35 U.S.C. 154(b) by 1120 days.

(21) Appl. No.: 12/142,260

(22) Filed: Jun. 19, 2008

(65) Prior Publication Data

US 2009/0298113 A1 Dec. 3, 2009

(30) Foreign Application Priority Data

May 28, 2008 (EP) .................................... 08157036

(51) Int. Cl.
*C12P 21/04* (2006.01)
(52) U.S. Cl. ..................................................... 435/70.3
(58) Field of Classification Search .................... None
See application file for complete search history.

(56) References Cited

FOREIGN PATENT DOCUMENTS

| | | |
|---|---|---|
| DE | 10055940 | 5/2002 |
| DE | 10317400 | 11/2004 |
| DE | 10317402 | 11/2004 |
| EP | 1361265 | 11/2003 |
| EP | 1927656 | 6/2008 |
| WO | WO-9200706 | 1/1992 |
| WO | WO-0238537 | 5/2002 |
| WO | WO-2004092726 | 10/2004 |

OTHER PUBLICATIONS

Hantash et al. Lasers in Surgery and Medicine. vol. 39 Issue 2 pp. 87-95 Feb. 2007.*
Guittet et al. IEEE Transactions on Biomedical Engineering, vol. 46, No. 6, Jun. 1999.*
Van Hall et al. Journal of Physiology (2002) vol. 543.3, pp. 1033 to 1046.*
Lu, Zhongfa et al., "Towards the development of a simplified long-term organ culture method for human scalp skin and its appendages under serum-free conditions," Experimental Dermatology, vol. 16, 2006, pp. 37-44.
Uphman, Elizabeth et al., "The relation of thickness of cutis and subcutis to hair slope in human," The anatomical record, vol. 61, No. 3, Feb. 1935, pp. 359-366.
Hori, Hiroyuki et al., "The thickness of human scalp: normal and bald," The Journal of investigative dermatology, vol. 58, No. 6, 1972, pp. 396-399.
Information letter n °2 of Jan. 2003 of Laboratory BIO-EC.
Serfling, Albrecht et al., "Treatment of a clinically relevant plant-pathogenic fungus with an agricultural azole causes cross-resistance to medical azoles and potentiates caspofungin efficacy," Antimicrobial agents and chemotherapy, vol. 51, No. 10, Oct. 2007, pp. 3672-3676.
Moon Se et al., "Induction of matrix metalloproteinase-1 (MMP-1) during epidermal vision of the stroma in human skin organ culture: keratinocyte stimulation of fibroblast MMP-1 production," British Journal of Cancer, vol. 85, No. 10, Oct. 2001, pp. 1600-1605.
Bolzinger et al., "Percutaneous release of caffeine from microemulsion emulsion and gel dosage forms," European Journal Pharmaceutics and Biopharmaceutics, vol. 68, Nov. 6, 2007, pp. 446-451.
Nakamura, Mashahiro et al., "Full-thickness human skin explants for testing the toxicity of topically applied chemicals," The Journal of investigative Dermatology, vol. 95, No. 3, Sep. 1990, pp. 326-332.
Franz Cells, "PermeGear static Franz Cells—Description and Figures", [cited Feb. 13, 2012].
Dipietro, Luisa A. et al., "Would Healing—Methods and Protocols," Methods in molecular medicine, 2003, pp. 305-308.
Tammi, Raija et al., "Skin organ culture: why?" International Journal of Dermatology, vol. 26, No. 3, Apr. 1987, pp. 150-160.
Agache, Pierre et al., "Measuring the skin," Springer, 2004, Ed. Springer, pp. 410-417.
Agache, Pierre et al., "Measuring the skin," Springer, 2004, Ed. Springer, pp. 241-243.
Waller et al., chapter 35, pp. 295-299, "A dermatological view; from physiology to therapy" 2011.
Uphman, Elizabeth et al., "The anatomical record," Feb. 28, 1935, [cited Feb. 7, 2012], available from: [http://onlinelibrary.wiley.com/doi/10.1002/ar.v61:3/issuetoc], pp. 1 and 3.
Otberg, Nina et al., "Variations of hair follicle size and distribution in different body sites," The Journal of investigative Dermatology, vol. 122, Jan. 2004, pp. 14-19.
Hantash, Basil M. et al., "Ex Vivo Histological Characterization of a Novel Ablative Fractional Resurfacing Device," Lasers in Surgery and Medicine, 39, 2007, pp. 87-95.
Agache, Pierre et al., "Measuring the Skin," Springer 2004, pp. 3-5.
Li, Lingna et al., "Hair shaft elongation, follicle growth, and spontaneous regression in long-term, gelatin sponge-supported histoculture of human scalp skin," Proc. Natl. Acad. Sci. USA, vol. 89, 1992 pp. 8764-8768.
Hunnius Pharmaceutisches Wörterbuch, 8. edition, 19989, p. 644.
Boisnic, S. et al., "Repair of UVA-Induced Elastic Fiber and Collagen Damage by 0.05% Retinaldehyde Cream in an ex vivo Human Skin Model," Dermatology, 1999, 199 (suppl. 1), pp. 43-48.
Notice of Opposition, European Application No. 08157036.8, dated Feb. 23, 2012.
Notice of Opposition, European Patent Application No. 08157036.8, dated Mar. 2, 2012.

* cited by examiner

*Primary Examiner* — Chris R Tate
*Assistant Examiner* — Douglas F White
(74) *Attorney, Agent, or Firm* — Connolly Bove Lodge & Hutz LLP

(57) ABSTRACT

The present invention relates to the use of an ex vivo human skin sample as a biological model, particularly for the assessment of pharmacological and cosmetic effects.

16 Claims, No Drawings

EX VIVO HUMAN SKIN MODEL

CROSS-REFERENCE TO PRIOR APPLICATION

The present application claims benefit of priority to EP 08 157 036.8, filed on May 28, 2008, the disclosure of which is incorporated herein by reference in its entirety.

The present invention relates to the use of a human skin sample as a skin model, particularly a biological model for assessing pharmacological, nutraceutical and cosmetic effects of compounds proposed for human body treatments.

The skin being the largest human organ, all substances intended for topical application thereon must undergo extensive testing to ensure there safety. However, testing substances on the human skin is only possible under a few exceptional circumstances. In the past, testing therefore had to be performed on animals. However, animal testing, i.e. performing tests on the skin of living animals, is undesired or even forbidden by law. There is thus a pressing need to develop skin models which circumvent the need to expose living animals to potentially hazardous substances.

Conventional skin models often rely on reconstituted human or animal skin. Frequently, monolayer cultures of selected skin cell types (e.g. fibroblasts) are grown in a culture medium and are charged with a substance the effects of which are to be assessed. However, such monolayer cultures do not allow to assess effects resulting from interaction of different cell types or resulting from three-dimensional cell interaction. In addition, the time required for establishing such cultures is considerably long. Monolayer skin cell cultures are thus deemed inadequate for faithfully modelling the effects of a substance on human skin.

Other models involve reconstructed skin models, consisting of a maximum of four different cell types, most commonly keratinocytes, melanocytes and fibroblasts (EpiSkin™ [L'Oréal, Paris, France], EpiDerm™ [MatTek, Ashland, USA], SkinEthic™ [SkinEthic, Nice, France]. Although these models are useful to study selected effects in the dermis or epidermis, they are not suitable for studying the whole range of possible interactions of a substance with human skin. Attempts to construct a full skill model in vitro have so far failed.

It has therefore been tried to establish a culturing system for intact skin samples or ex vivo human or animal skin samples. One major disadvantage of existing ex vivo skin models is their too limited viability.

The maximum time of viability of e.g. ex vivo pig skin samples is currently limited to seven days (cf. e.g. DE 10317400A1). This maximum time of viability requires users to frequently obtain new skin samples, thereby reducing reproducibility, requiring frequent calibrations and, since the decline in viability can even affect short-term substance assays, requires a high precision and great care when analysing measured effects. Related thereto, DE 10317402 describes a method for manufacturing male ex vivo pig skin. Fat tissue is cut off and the remaining epidermis and dermis are placed in a cultivation medium such that the epidermis is exposed to air. The publications do not provide any indication on the viability of the skin samples after seven days. Also, by removal of fat tissue significant parts of the hair bulb, apocrine and eccrine glands get lost, impairing skin sample viability.

There is thus a great need for a skin model for modelling a selected effect of a selected treatment of human skin. Preferably, the model should allow for a skin sample viability of >7 days, more preferably of at least 10 days, and even more preferably of at least 15 days after explantation. Also, the model should allow to assess a huge variety of effects of human skin treatments. The model should be easy to use and should allow for a high prognostic value regarding the effects of a treatment of human skin.

According to the present invention, an ex vivo human skin sample is therefore used as a model for human or animal skin, said sample comprises an epidermis, dermis and a subcutis ("fat") layer. Within the scope of the present invention, a skin sample is an isolated body of skin consisting of an epidermal layer, a dermal layer ("dermis", sometimes also termed "corium"), and a subcutis layer, preferably containing at least one complete/fully preserved and structurally intact hair bulb.

According to the present invention, the ex vivo human skin sample comprises a cell layer of epidermis cells and corresponding tissues structure, preferably a stratum corneum section and a stratum basale section. Further, the skin sample comprises a dermal layer between the epidermis and the subcutis layer. The subcutis layer comprises cells of a human subcutis, preferably adipose tissue cells, and preferably also has a subcutis tissue structure. The human skin sample does not comprise a complete human skin subcutis; it is sufficient that the human sample comprises a subcutis layer with an average thickness of 0.5 to 5 mm, preferably the subcutis layer has a thickness of at least 1 mm and even more preferred a thickness of 1 to 3 mm.

So far, the beneficial effects of the presence of a subcutis layer for human skin sample viability, reproducibility of skin sample test results and significance of skin sample test results, e.g. their value for predicting skin reactions of a human being subjected to the same treatment as the skin sample, had not been described or anticipated. Instead, typically the subcutis layer of prior art ex vivo human skin samples was fully removed.

It has now been found that contrary to present day believe, the presence of a fat layer (subcutis layer) in ex vivo human skin samples beneficially increases sample viability, test reproducibility and prognostic value. An ex vivo human skin sample according to the present invention is highly viable and fully functional for more than 7 days, usually and preferably for more than 10 days, and even more preferably for more than 15 days, after explantation from a human being (donator).

Surprisingly, it has additionally now been found that sample viability is further correlated to hair follicle density. A skin sample having a hair follicle density of at least one, preferably 2-14 (primary), more preferably 2-10 (primary) hair follicles per $cm^2$ shows even improved viability and functionality, i.e. for more than 8 days, preferably for more than 12 days, and even more preferably for more than 18 days after explantation from a human being, and allows for the assessment of a whole range of different biological parameters in an easy manner, as is described in greater detail below.

Further, part of the hair follicles are in contact with the outer layer of the subcutis in the human skin. Thus, the maintenance of a subcutis layer in the ex vivo human skin sample is necessary in order to ascertain a certain density of living hair follicles in the same.

Thus, it is particularly preferred that the skin sample of the present invention comprises at least one primary hair follicle, even more preferred at least two, three, four, five or more primary hair follicles. It is presently believed that skin sample viability is beneficially increased by interaction between hair follicle cells and respective surrounding cells of the skin sample.

Thus, it is particularly preferred that the human skin sample according to the present invention comprises at least one, preferably at least two, three or more viable (primary)

hair follicles. For the present invention, a hair follicle is deemed to be viable if it was able to produce a skin hair in the human and is structurally intact, that is to say not disrupted or incomplete, in the skin sample. A hair follicle is deemed to be viable according to the present invention if the minimum distance between the hair bulb and the nearest edge of the skin sample is at least 1 mm and even more preferably 1 to 3 mm.

According to the invention, a skin sample is viable and completely functional as long as both of the following conditions are fulfilled:

a) the skin sample contains at least 1.5% of skin cells stainable with the proliferation marker Ki-67, and
b) the percentage of skin cells of the skin sample stainable with the proliferation marker Ki-67 is more than 25% compared to the skin cells stainable with the proliferation marker Ki-67 at the start of the incubation.

Preferably, the skin sample has a hair follicle density of at least two hair follicles per cm$^2$, more preferably of 2-14, more preferably 2-10, hair follicles per cm$^2$. Such skin samples have proven to be particularly long viable. They are thus easy to handle and do not require frequently obtaining new skin samples and new sample calibrations.

According to the invention, ex vivo human skin samples are preferably taken from abdomen, thigh or breast, more preferably from abdomen or breast, most preferably from abdomen. Breast skin is less preferred than abdomen skin since breast skin is not always suitable for all types of assessments listed below. According to the invention, ex vivo human skin samples a preferably taken from female humans. According to the invention, ex vivo human skin samples are preferably taken from donors being 18-60 years of age. Also according to the invention, the donor is preferably alive at the time the skin sample is taken, or at least blood circulation in the donor body has not stopped for more than 10 minutes before taking of the skin sample.

Preferably, the skin sample has a thickness of at least 2 mm, preferably of at least 3 mm and more preferred of 4-5 mm. In addition, the skin sample preferably has an epidermis surface area of at least 9 mm$^2$ and more preferred of 16-25 mm$^2$. Skin samples of these sizes have proven to be particularly viable. Thus, skin samples sizes with the following dimensions are preferred (length×width×thickness): (5-10)×(5-10)×(2-5) mm, preferably (8-10)×(8-10)×(3-4) mm. These sample sizes allow to completely include structurally intact, functioning hair follicles and hairs in the sample.

Thus, it is particularly preferred for a skin sample with an epidermis surface area of 64-100 mm$^2$ to comprise at least one hair follicle, more preferably at least two hair follicles, and still more preferred at least three hair follicles, as described above.

Skin samples are preferably prepared from larger skin patches taken from a donor. The area of the skin to be excised is preferably washed with distilled water and then dried, preferably with sterile gauzes. Afterwards, the hair shafts are cut be using an electric clipper at a length of 1-2 mm. Preferably, the skin is not injured during clipping. It is further preferred that all skin where a skin patch is to be taken from is subsequently washed by using a surgical soap; the soap being removed from the skin by plugging with sterile gauzes soaked in distilled water. Afterwards, the skin is further cleaned with chlorhexidine and then dried with sterile gauzes. Lastly, the skin is restored by using a physiological saline solution.

The skin patches to be excised are carved with a scalpel in order to obtain lens-shaped patches. The patches preferably have a dimension of 5-8 cm (length) and 2-5 cm (width.), most preferably 6 cm×4 cm. It is convenient to perform the excision by two cuts that follow the edges of the lens-shaped skin patch to be excised.

The skin patch is then lifted carefully, e.g. by the use of forceps, and is gently detached from the muscle. The skin patch then includes epidermis, dermis and subcutis fat layer. The fat layer is preferably further reduced to a maximum thickness of 3 mm. It has been found that a fat layer of this thickness favourably allows nutrition of the tissue from culture media.

Once excised, the skin patches are placed in a 50 ml tube containing 40 ml of transport medium and maintained at 4° C. until the patches arrives at the laboratory to be further processed. It has been found that this medium provides an effective protection of skin patches from bacterial contamination during the transfer to the laboratory, and it also protecting the skin patches tissue characteristics.

A suitable transport medium is (Dulbecco Modified Eagle Medium (DMEM) with added penicillin (100 U/ml) and streptomycin (100 µg/ml).

Most preferably, the excised skin patch is treated for not more than 4 hours, preferably not more than 3 hours with transport medium. Fast processing of the skin patches to obtain skin samples aids in ensuring minimal or no skin degeneration.

For preparing skin samples for the assessment of a selected effect of a skin treatment, skin patches are transferred to a culture medium. The culture medium preferably is free of fetal calf serum (FCS), and even more preferably is a complex culture medium like William's E medium. Of course, the culture medium composition is selected by the skilled person in view of the treatment and effect to assess. Thus, a generally less preferred culture medium may be suitable under special circumstances. The culture medium can be supplemented by compounds known to improve the proliferation of skin and hair cells as e.g. vitamins or zinc salts.

When preparing skin samples from skin patches, generally the edges of skin patches are cut and discarded. The remaining skin sample is placed on a sterile support, preferably cork, and cut to the desired sizes as given above, preferably to a size of 8×8×4 mm (length×width×thickness).

Skin samples are preferably placed in a culture medium with the epidermis surfacing the air above the culture medium and the subcutaneous fat and dermis layers being completely immersed in the culture medium. It is however preferred to place skin samples on a sterile support like a cotton pad, will the support is soaked with culture medium, and the skin sample being oriented such that the fat and dermis layer are directed to the support and the epidermis being directed upwardly. Preferably, the sterile support and particularly the soaked cotton pad is replaced every 3 days. It is further preferred to place two or three skin samples on one support. The support is preferably located inside a well of a conventional-type six well culture plate.

The skin samples can be used for excising/modeling a variety of treatments, among which are:

a) effects of exposition of skin samples to substances, the substances being applied topically to the skin sample and/or systemically to the skin sample by mixing with the culture medium; or
b) effects of skin sample irradiation.

Preferably, the skin samples are used for the assessment of one or more of the following effects, preferably caused by the application of a putatively effect-causing substance or other treatment:

modulation of skin and/or hair pigmentation,
modulation of hair growth, modulation of skin and/or hair viability and/or proliferation,
modulation of fat metabolism,
anti-cellulite properties of substances,
slimming,
anti-aging effects, particularly by fat cell stimulation
allergenic potential and/or irritation,
UV protection, particularly UV erythema prevention, alleviation and healing,
effects induced by visible light or infra red light
effects caused by mechanical stress as e.g. abrasion or pressure
modulation of connecting tissue properties, particularly for the assessment of anti-wrinkle properties of substances,
anti-oxidative effects,
wound healing,
modulation of skin barrier function,
modulation of ion channels, especially neurofunctional channels and preferably channels activated by GABA, glutamate, acetylcholine, serotonin, adrenalin and ATP, and temperature sensitive channels (e.g. TRPM8, TRPV3, TRPV4, TRPV1, ANKTM/TRPA1, TRPV2),
immunestimulation, immunesuppression,
sebum stimulation, sebum suppression,
anti-microbial effectiveness, particularly effectiveness of anti-acne, anti-dandruff, deodorant or preservative materials,
sweat secretion decrease,
substantivity of materials on a skin surface,
film forming effectiveness,
modulation of skin and hair thickness,
moisturization,
phototoxicity,
skin metabolism
penetration properties
release properties from formulations The skin model of the invention is particularly suitable to assess the effects of
flavour compounds, particularly allergenic potential assessment,
fragrance compounds, particularly for substantivity and allergenic potential assessment,
pharmaceutical compounds, particularly for skin penetration, skin damage alleviation and skin damage healing,
insect repellents, particularly for skin penetration and skin damage,
make up compounds, particularly pigments, particularly for skin penetration, skin damage or skin adhesiveness,
hair care ingredients,
nutraceuticals, dietary supplements or functional food.

The substances the effects of which are to be assessed by the skin model, are applied topically by application to the epidermis, or systemically by addition to a cultivation medium. The substances can be applied in any form, including application as a pure substance, or a mixture with one or more other substances (that may or may not have effects on a skin model). The substance or substances can be applied as a solid, a gel, a cream or other multi-phase composition, a liquid, a foam or a gas.

The substance(s) and formulations to be tested (hereinafter: "formulation") on the skin model according to the invention can take the form of soap, syndet, liquid washing, shower and bath preparation, emulsion (as solution, dispersion, suspension, cream, lotion or milk, depending on preparative method and ingredients, of the type W/O, O/W or multiple emulsion, PIT emulsion, emulsion foam, microemulsion, nanoemulsion, Pickering emulsion), ointment, paste, gel (including hydrogel, hydrodispersion gel, oleogel), oil, toner, balsam, serum, powder, eau de toilette, eau de Cologne, perfume, wax, stick, roll-on, (pump) spray, aerosol (foaming, non-foaming or after-foaming), foot care product (including keratolytics, deodorant), pre-shave or after-shave (balm, lotion), depilatory product, hair care product, e.g. shampoo (incl. 2-in-1 shampoo), conditioner, hair treatment, hair tonic, hair rinse, hair cream, pomade, perming and fixing product, hair straightening product (defrizzer, relaxer), hair strengthener, styling aid (e.g. gel or wax), bleach, hair dye (e.g. temporary, direct, semipermanent, permanent hair dye), nail care product, e.g. nail varnish and nail varnish remover, deodorant and/or antiperspirant, mouthwash, make-up, make-up remover or decorative cosmetic (e.g. powder, eye shadow, kajal stick, lipstick).

It can be advantageous to provide the formulations to be applied to the skin model according to the present invention in encapsulated form, e.g. in gelatin, wax materials, liposomes, cellulose capsules or cyclodextrin capsules.

Other conventional cosmetic auxiliary substances and additives can be present in formulations in amounts advantageously of 5-99 wt. %, preferably of 10-80 wt. %, based on the total weight of the mixture. The formulations can also contain water in an amount of up to 99.99 wt. %, preferably of 5-80 wt. %, based on the total weight of the formulation.

The formulations can be or contain cosmetic auxiliary substances and additives such as those conventionally used in cosmetic preparations, e.g. sunscreens, preservatives, bactericides, fungicides, virucides, cooling substances, insect repellents (e.g. DEET, IR 3225, Dragorepel), plant extracts, antiinflammatory substances, wound healing accelerators (e.g. chitin or chitosan and its derivatives), film-forming substances (e.g. polyvinylpyrrolidones or chitosan or its derivatives), customary antioxidants, vitamins (e.g. vitamin C and derivatives, tocopherols and derivatives, vitamin A and derivatives), 2-hydroxycarboxylic acids (e.g. citric acid, malic acid, L-, D- or DL-lactic acid), skin colourants (e.g. walnut extracts or dihydroxyacetone), active ingredients for promoting hair growth (e.g. minoxidil, diphencyprone, hormones, finasteride, phytosterols such as beta-sitosterol, biotin, or extracts of *Cimicifuga racemosa, Eugenia caryophyllata* or *Hibiscus rosasinensis*, barley, hops, or rice or wheat hydrolysates), skin care products (e.g. cholesterol, ceramides, pseudoceramides), softening, moisturizing and/or moisture-retaining substances (e.g. glycerol or urea), fats, oils, saturated fatty acids, monounsaturated or polyunsaturated fatty acids, α-hydroxy acids, polyhydroxy fatty acids or their derivatives (e.g. linoleic acid, α-linolenic acid, γ-linolenic acid or arachidonic acid and their respective natural or synthetic esters), waxes or other conventional constituents of a cosmetic or dermatological formulation, such as alcohols, polyols, polymers, foam stabilizers, electrolytes, organic solvents, silicone derivatives or chelating agents (e.g. ethylenediaminetetraacetic acid and derivatives), antidandruff substances (e.g. climbazole, ketoconazole, piroctonoleamine, zinc pyrithione), hair care products, perfumes, antifoams, dyestuffs, pigments with a colouring action, thickeners (advantageously silicon dioxide, aluminium silicates such as bentonites, polysaccharides or their derivatives, e.g. hyaluronic acid, guar kernel flour, xanthan gum, hydroxypropyl methyl cellulose or allulose derivatives, particularly advantageously polyacrylates such as carbopols, or polyurethanes), surface-active substances, emulsifiers, plant parts and plant extracts (e.g. arnica, aloe, beard lichen, ivy, stinging nettle, ginseng, henna, chamomile, marigold, rosemary, sage, horsetail or thyme), animal extracts, e.g. royal jelly or propolis, proteins, protein hydrolysates, yeast extracts, hop and wheat extracts, peptides or thymus extracts.

The amounts of cosmetic or dermatological auxiliary substances and additives and perfume to be used can readily be determined by those skilled in the art on a simple trial-and-error basis, as a function of the particular type of product.

Advantageously the formulations be or contain at least one UVA filter and/or at least one UVB filter and/or at least one inorganic pigment. The mixtures can take a variety of forms, e.g. those conventionally used for sunscreen preparations for protecting the skin and hair from ultraviolet radiation. They can thus form e.g. a solution, an emulsion of the water-in-oil (W/O) type or oil-in-water (O/W) type, or a multiple emulsion, for example of the water-in-oil-in-water (W/O/W) type, a gel, a hydrodispersion, a solid stick or else an aerosol. The total amount of filter substances is from 0.01 wt. % to 40 wt. %, preferably from 0.1% to 10 wt. % and particularly preferably from 1.0 to 5.0 wt. %, based on the total weight of the mixture, in order to provide cosmetic mixtures (preparations).

Examples of Advantageous UV Filters Are:
p-aminobenzoic acid
ethyl p-aminobenzoate, ethoxylated (25 mol)
2-ethylhexyl p-dimethylaminobenzoate
ethyl p-aminobenzoate, N-propoxylated (2 mol)
glyceryl p-aminobenzoate
homomenthyl salicylate (homosalate) (Neo Heliopan®HMS)
2-ethylhexyl salicylate (Neo Heliopan®OS)
triethanolamine salicylate
4-isopropylbenzyl salicylate
menthyl anthranilate (Neo Heliopan®MA)
ethyl diisopropylcinnamate
2-ethylhexyl p-methoxycinnamate (Neo Heliopan®AV)
methyl diisopropylcinnamate
isoamyl p-methoxycinnamate (Neo Heliopan®E 1000)
p-methoxycinnamic acid diethanolamine salt
isopropyl p-methoxycinnamate
2-ethylhexyl 2-cyano-3,3-diphenylacrylate (Neo Heliopan®303)
ethyl 2-cyano-3,3'-diphenylacrylate
2-phenylbenzimidazolesulfonic acid and salts (Neo Heliopan®Hydro)
3-(4'-trimethylammonium)benzylidenebornan-2-one methylsulfate
terephthalylidenedibornanesulfonic acid and salts (Mexoryl®SX)
4-t-butyl-4'-methoxydibenzoylmethane (avobenzone)/(Neo Heliopan®357)
β-imidazol-4(5)-acrylic acid (urocanic acid)
2-hydroxy-4-methoxybenzophenone (Neo Heliopan®BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octyloxybenzophenone
2-hydroxy-4-methoxy-4'-methylbenzophenone
3-(4'-sulfo)benzylidenebornan-2-one and salts
3-(4'-methylbenzylidene)-d,l-camphor (Neo Heliopan®MBC)
3-benzylidene-d,l-camphor
4-isopropyldibenzoylmethane
2,4,6-trianilino(p-carbo-2'-ethylhexyl-1'-oxy)-1,3,5-triazine
phenylenebisbenzimidazyltetrasulfonic acid disodium salt (Neo Heliopan®AP)
2,2'-(1,4-phenylene)bis(1H-benzimidazole-4,6-disulfonic acid)monosodium salt
N-[(2 and 4)-[2-(oxoborn-3-ylidene)methyl]benzyl]acrylamide polymer
phenol,2-(2H-benzotriazol-2-yl)-4-methyl-6-(2-methyl-3-(1,3,3,3-tetramethyl-1-((trimethylsilyl)oxy)disiloxanyl)propyl) (Mexoryl®XL)
4,4'-[(6-[4-(1,1-dimethyl)aminocarbonyl)phenylamino]-1,3,5-triazine-2,4-diyldiimino]bis(benzoic acid 2-ethylhexyl ester) (Uvasorb®HEB)
2,2'-methylenebis(6-(2H-benztriazol-2-yl)-4-(1,1,3,3-tetramethylbutyl)phenol) (Tinosorb®M)
2,4-bis[4-(2-ethylhexyloxy)-2-hydroxyphenyl]-1,3,5-triazine
benzylidene malonate polysiloxane (Parsol®SLX)
glyceryl ethylhexanoate dimethoxycinnamate
disodium 2,2'-dihydroxy-4,4'-dimethoxy-5,5'-disulfobenzophenone
dipropylene glycol salicylate
sodium hydroxymethoxybenzophenonesulfonate
4,4',4-(1,3,5-triazine-2,4,6-triyltriimino)tris(benzoic acid 2-ethylhexyl ester) (Uvinul®T150)
2,4-bis[{4-(2-ethylhexyloxy)-2-hydroxy}phenyl]-6-(4-methoxyphenyl)-1,3,5-triazine (Tinosorb®S)
2,4-bis[{(4-(3-sulfonato)-2-hydroxypropoxy)-2-hydroxy}phenyl]-6-(4-methoxyphenyl)-1,3,5-triazine sodium salt
2,4-bis[{(3-(2-propoxy)-2-hydroxypropoxy)-2-hydroxy}phenyl]-6-(4-methoxyphenyl)-1,3,5-triazine
2,4-bis[{4-(2-ethylhexyloxy)-2-hydroxy}phenyl]-6-[4-(2-methoxyethylcarbonyl)phenylamino]-1,3,5-triazine
2,4-bis[{4-(3-(2-propoxy)-2-hydroxypropoxy)-2-hydroxy}phenyl]-6-[4-(2-ethylcarboxy)phenylamino]-1,3,5-triazine
2,4-bis[{4-(2-ethylhexyloxy)-2-hydroxy}phenyl]-6-(1-methylpyrrol-2-yl)-1,3,5-triazine
2,4-bis[{4-tris(trimethylsiloxysilylpropoxy)-2-hydroxy}phenyl]-6-(4-methoxyphenyl)-1,3,5-triazine
2,4-bis[{4-(2"-methylpropenyloxy)-2-hydroxy}phenyl]-6-(4-methoxyphenyl)-1,3,5-triazine
2,4-bis[{4-(1',1',1',3',5',5',5'-heptamethylsiloxy-2"-methylpropoxy)-2-hydroxy}phenyl]-6-(4-methoxyphenyl)-1,3,5-triazine
hexyl 2-(4-diethylamino-2-hydroxybenzoyl)benzoate (Uvinul® A Plus)
indanylidene compounds according to DE 100 55 940 (=WO 02/38537)

The following UV absorbers are particularly suitable for combination:
p-aminobenzoic acid
3-(4'-trimethylammonium)benzylidenebornan-2-one methylsulfate
homomenthyl salicylate (Neo Heliopan®HMS)
2-hydroxy-4-methoxybenzophenone (Neo Heliopan®BB)
2-phenylbenzimidazolesulfonic acid (Neo Heliopan®Hydro)
terephthalylidenedibornanesulfonic acid and salts (Mexoryl®SX)
4-tert-butyl-4'-methoxydibenzoylmethane (Neo Heliopan®357)
3-(4'-sulfo)benzylidenebornan-2-one and salts
2-ethylhexyl 2-cyano-3,3-diphenylacrylate (Neo Heliopan®303)
N-[(2 and 4)-[2-(oxoborn-3-ylidene)methyl]benzyl]acrylamide polymer
2-ethylhexyl p-methoxycinnamate (Neo Heliopan®AV)
ethyl p-aminobenzoate, ethoxylated (25 mol)

isoamyl p-methoxycinnamate (Neo Heliopan®E1000)

2,4,6-trianilino(p-carbo-2'-ethylhexyl-1'-oxy)-1,3,5-triazine (Uvinul®T150)

phenol,2-(2H-benzotriazol-2-yl)-4-methyl-6-(2-methyl-3-(1,3,3,3-tetramethyl-1-((trimethylsilyl)oxy)disiloxanyl)-propyl) (Mexoryl®XL)

4,4'-[(6-[4-(1,1-dimethyl)aminocarbonyl)phenylamino]-1,3,5-triazine-2,4-diyldiimino]bis(benzoic acid 2-ethylhexyl ester) (Uvasorb®HEB)

3-(4'-methylbenzylidene)-d,l-camphor (Neo Helipan®MBC)

3-benzylidenecamphor 2-ethylhexyl salicylate (Neo Helipan®OS)

2-ethylhexyl 4-dimethylaminobenzoate (Padimate O)

hydroxy-4-methoxybenzophenone-5-sulfonic acid and Na salt 2,2'-methylenebis(6-(2H-benztriazol-2-yl)-4-(1,1,3,3-tetramethylbutyl)phenol) (Tinosorb®M)

phenylenebisbenzimidazyltetrasulfonic acid disodium salt (Neo Heliopan®AP)

2,4-bis[{4-(2-ethylhexyloxy)-2-hydroxy}phenyl]-6-(4-methoxyphenyl)-1,3,5-triazine (Tinosorb®S)

benzylidene malonate polysiloxane (Parsol®SLX)

menthyl anthranilate (Neo Heliopan®MA)

hexyl 2-(4-diethylamino-2-hydroxybenzoyl)benzoate (Uvinul® A Plus)

indanylidene compounds according to DE 100 55 940 (=WO 02/38537)

Advantageous inorganic light-protecting pigments are finely disperse metal oxides and metal salts, for example titanium dioxides, zinc oxide (ZnO), iron oxides (e.g. $Fe_2O_3$), aluminium oxide ($Al_2O_3$), cerium oxides (e.g. $Ce_2O_3$), manganese oxides (e.g. MnO), zirconium oxide ($ZrO_2$), silicon oxide ($SiO_2$), mixed oxides of the corresponding metals, and mixtures of such oxides, barium sulfate and zinc stearate. Particularly preferred pigments are those based on $TiO_2$ or zinc oxide. In preferred embodiments the particles have a mean diameter of less than 100 nm, preferably of between 5 and 50 nm and particularly preferably of between 15 and 30 nm. They can have a spherical shape, but it is also possible to use particles with an ellipsoid shape or a shape that differs from spherical in some other way. The pigments can also be surface-treated, i.e. hydrophilized or hydrophobized. Typical examples are coated titanium dioxides, e.g. titanium dioxide T 805 (Degussa) or Eusolex® T2000 (Merck), or coated zinc oxide, e.g. zinc oxide NDM, suitable hydrophobic coating agents being primarily silicones and especially trialkoxyoctylsilanes or simethicones. So-called micropigments or nanopigments are preferably used in sunscreen products, zinc micropigments or nanopigments being particularly preferred.

The total amount of inorganic pigments, especially hydrophobic inorganic micropigments, in the finished cosmetic or dermatological formulations advantageously ranges from 0.1 to 30 wt. %, preferably from 0.1 to 10.0 and particularly preferably from 0.5 to 6.0 wt. %, based on the total weight of the formulations.

Anti-irritants such as (alpha-)bisabolol can also be used in or as formulations to be tested with the aid of the skin model according to the invention. Anti-irritants can be any anti-inflammatory or redness-alleviating and antipruritic substances that are suitable or customary for cosmetic and/or dermatological applications. Preferred anti-inflammatory or redness-alleviating and antipruritic substances (anti-irritants) are steroidal anti-inflammatory substances of the corticosteroid type, e.g. hydrocortisone, dexamethasone, dexamethasone phosphate, methylprednisolone or cortisone, it being possible to extend the list by adding other steroidal anti-inflammatories. Non-steroidal anti-inflammatories can also be used. The following may be mentioned as examples: oxicams such as piroxicam or tenoxicam; salicylates such as aspirin, Disalcid, Solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen or benoxaprofen; or pyrazoles such as phenylbutazone, oxyphenylbutazone, febrazone or azapropazone. Natural anti-inflammatory or redness-alleviating and antipruritic substances can be used as alternatives, possibilities being plant extracts, special potent plant extract fractions, and high-purity active substances isolated from plant extracts. Particular preference is given to extracts, fractions and active substances from chamomile, Aloe vera, *Commiphora* species, *Rubia* species, *Echinacea* species, willows, willow herb, oats, black and green tea, gingko, coffee, pepper, redcurrant/blackcurrant, tomato, vanilla and almonds, as well as pure substances such as, inter alia, apigenin-7-glucoside, boswellic acid, phytosterols, glycyrrhizinic acid, glabridin or licochalcone A.

In terms of the invention, particular preference is given to panthenol, boswellic acid and extracts and isolated high-purity active substances from oats (e.g. avenanthramides) and *Echinacea*, and mixtures thereof.

The formulations can also be or contain antioxidants, it being possible to use any antioxidants suitable or customary for cosmetic and/or dermatological applications. The antioxidants are advantageously selected from the group comprising amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl, lauryl, palmitoyl, oleyl, γ-linoleyl, cholesteryl and glyceryl esters) and their salts, dilauryl thiodipropionate, distearyl thiodipropionate, thiodipropionic acid and derivatives thereof (esters, ethers, peptides, lipids, nucleotides, nucleosides and salts), sulfoximine compounds (e.g. buthionine sulfoximine, homocysteine sulfoximine, buthionine sulfone, penta-, hexa-, heptathionine sulfoximine) in very small tolerable doses, (metal) chelators, e.g. α-hydroxy fatty acids, palmitic acid, phytic acid, lactoferrin, α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbylphosphate, ascorbyl acetate, ascorbyl glycosides such as 6-O-acyl-2-O-α-D-glucopyranosyl-L-ascorbic acid, 6-O-acyl-2-O-β-D-glucopyranosyl-L-ascorbic acid, 2-O-α-D-glucopyranosyl-L-ascorbic acid or 2-O-β-D-glucopyranosyl-L-ascorbic acid), tocopherols and derivatives thereof (e.g. vitamin E acetate), vitamin A and derivatives thereof (vitamin A palmitate), coniferyl benzoate from benzoin, rutic acid and derivatives thereof, alpha-glycosylrutin, quercetin and derivatives thereof, rosmaric acid, carnosol, carnosolic acid, resveratrol, caffeic acid and derivatives thereof, sinapic acid and derivatives thereof, ferulic acid and derivatives thereof, furfurylideneglucitol, curcuminoids, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$), selenium and derivatives thereof (e.g. selenium methionine), stilbenes and derivatives thereof (e.g. stilbene oxide, trans-stilbene oxide), derivatives (salts, esters, ethers, sugars, nucleotides, nucleosides, peptides and lipids) of said active substances, or antioxidative extracts or fractions of plants such as green tea, rooibos, honeybush, grape, rosemary, sage, balm, thyme, lavender, olive, oats, cacao, gingko, ginseng, liquorice, honeysuckle, Sophora, Pueraria, *Pinus*, Citrus, *Phyllanthus emblica* or St John's wort.

The amount of antioxidants (one or more compounds) in the formulations is preferably 0.01 to 20 wt. %, particularly preferably 0.05-10 wt. % and very particularly preferably 0.2-5 wt. %, based on the total weight of the preparation.

If vitamin E and/or its derivatives represent the antioxidant(s), their respective concentrations are advantageously chosen from the range between 0.001 and 10 wt. %, based on the total weight of the formulation.

If vitamin A or vitamin A derivatives, or carotenes or their derivatives, represent the antioxidant(s), their respective concentrations are advantageously chosen from the range between 0.001 and 10 wt. %, based on the total weight of the formulation.

The (cosmetic) formulations can also be or contain active substances and active substance combinations for combating skin ageing and wrinkling. It is possible here, according to the invention, to use any active substances for combating skin ageing and wrinkling that are suitable or customary for cosmetic and/or dermatological applications. In this respect, advantageous active substances for combating skin ageing and wrinkling are soya protein or protein hydrolysates, soya isoflavones, hydrolysed rice protein, hydrolysed hazelnut protein, oligopeptides from hydrolysed *Hibiscus esculentus* extract, wheat protein, β-glucans, e.g. from oats, and derivatives thereof, glycoproteins, ursolic acid and its salts, betulin, betulinic acid and its salts, retinol, retinol palmitate, propyl gallate, precocenene, 6-hydroxy-7-methoxy-2,2-dimethyl-1(2H)-benzopyran, 3,4-dihydro-6-hydroxy-7-methoxy-2,2-dimethyl-1(2H)-benzopyran, creatine, or other synthetic or natural active substances for combating skin ageing and wrinkling, it also being possible for the latter to be used in the form of an extract of plants such as green tea, *Rubus fruticosus, Sanguisorba officinalis, Centella asiatica, Ribes nigrum, Passiflora incarnata, Phyllanthus emblica*, okra, algae, evening primrose, rosemary, sage, *Echinacea*, birch, apple or soya.

β-Glucan is particularly preferably used as another active substance for combating skin ageing; 1,3-1,4-linked β-glucan from oats, *Rubus fruticosus* extract or wheat protein is very particularly preferred.

Formulations in the form of a cosmetic preparation can advantageously also be or contain moisturizers. The following substances are examples of moisturizers used: sodium lactate, urea and urea derivatives, alcohols, glycerol, diols such as propylene glycol, 1,2-pentanediol, 1,2-hexanediol and 1,2-octanediol, collagen, elastin or hyaluronic acid, diacyl adipates, petrolatum, urocanic acid, lecithin, panthenol, phytantriol, lycopene, (pseudo)ceramides, glycosphingolipids, cholesterol, phytosterols, chitosan, chondroitin sulfate, lanolin, lanolin esters, amino acids, alpha-hydroxy acids (e.g. citric acid, lactic acid, malic acid) and derivatives thereof, mono-, di- and oligosaccharides such as glucose, galactose, fructose, mannose, fruit sugar and lactose, polysugars such as β-glucans, especially 1,3-1,4-β-glucan from oats, alpha-hydroxy fatty acids, triterpene acids such as betulinic acid or ursolic acid, and extracts from micro- or macroalgae.

The formulations can also be or used together with osmolytes. The following may be mentioned as examples of osmolytes: substances from the group comprising sugar alcohols (myoinositol, mannitol, sorbitol), quaternary amines such as taurine, choline, betaine, betaine glycine and ectoine, diglyceryl phosphate, phosphorylcholine, glycerophosphorylcholine, amino acids such as glutamine, glycine, alanine, glutamate, aspartate or proline, phosphatidylcholine, phosphatidylinositol, inorganic phosphates, and polymers of said compounds such as proteins, peptides, polyamino acids and polyols. All osmolytes have a skin-moisturizing effect at the same time.

Preferably, formulations can also be or contain active substances which stimulate skin and hair tinting or bronzing in a chemical or natural way, thereby achieving a more rapid action based on synergistic effects. Particularly preferably, said substances are substrates or substrate analogues of tyrosinase, such as L-tyrosine, L-DOPA or L-dihydroxyphenylalanine, stimulators of tyrosinase activity or expression, such as theophylline, caffeine, proopiomelanocortin peptides such as ACTH, alpha-MSH, their peptide analogues and other substances that bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, flavonoids, flavanone glycosides such as naringin and hesperidin, melanin derivatives such as Melasyn-100 and MelanZe, diacylglycerols, aliphatic or cyclic diols, psoralenes, prostaglandins and their analogues, adenylate cyclase activators, and compounds which activate the transfer of melanosomes into keratinocytes, such as serine proteases or PAR-2 receptor agonists, extracts of plants and plant parts of *Chrysanthemum* species and *Sanguisorba* species, walnut extracts, urucum extracts, rhubarb extracts, erytrulose and dihydroxyacetone.

The formulations can advantageously be or be used in combination with skin-lightening substances. Any skin-lightening substances that are conventional or customary for cosmetic and/or dermatological applications can be used according to the invention. Advantageous skin-lightening substances in this respect are kojic acid (5-hydroxy-2-hydroxymethyl-4-pyranone), kojic acid derivatives, e.g. kojic acid dipalmitate, arbutin, ascorbic acid, ascorbic acid derivatives, hydroquinone, hydroquinone derivatives, resorcinol, sulfur-containing molecules, e.g. glutathione or cysteine, alpha-hydroxy acids (e.g. citric acid, lactic acid, malic acid) and derivatives thereof, N-acetyltyrosine and derivatives, undecenoylphenylalanine, gluconic acid, 4-alkylresorcinols, chromone derivatives such as aloesin, flavonoids, thymol derivatives, 1-aminoethylphosphinic acid, thiourea derivatives, ellagic acid, nicotinamide, zinc salts such as zinc chloride or gluconate, thujaplicin and derivatives, triterpenes such as maslinic acid, sterols such as ergosterol, benzofuranones such as senkyunolide, vinyl- and ethylguaiacol, inhibitors of nitrogen oxide synthesis, e.g. L-nitroarginine and derivatives thereof, 2,7-dinitroindazole or thiocitrulline, metal chelators (e.g. α-hydroxy fatty acids, palmitic acid, phytic acid, lactoferrin, humic acid, bile acid, bile extracts, bilirubin, biliverdin, EDTA, EGTA and derivatives thereof), retinoids, soya milk, serine protease inhibitors, lipoic acid or other synthetic or natural active substances for lightening the skin and hair, the latter also being used in the form of plant extracts, e.g. bearberry extract, rice extract, liquorice root extract or constituents obtained therefrom by enrichment, such as glabridin or licochalcone A, *Artocarpus* extract, extract of *Rumex* and *Ramulus* species, extracts of pine species (*Pinus*) and extracts of *Vitis* species or stilbene derivatives obtained therefrom by enrichment, and extracts of *Saxifraga*, mulberry, *Scutelleria* and/or grapes.

Formulations in the form of cosmetic preparations can also contain anionic, cationic, non-ionic and/or amphoteric surfactants, especially if crystalline or microcrystalline solids, for example inorganic micropigments, are to be incorporated into the mixtures.

Anionic surfactants normally have carboxylate, sulfate or sulfonate groups as functional groups. In aqueous solution they form negatively charged organic ions in an acidic or neutral medium. Cationic surfactants are almost exclusively characterized by the presence of a quaternary ammonium group. In aqueous solution they form positively charged organic ions in an acidic or neutral medium. Amphoteric surfactants contain both anionic and cationic groups and accordingly behave as anionic or cationic surfactants in aqueous solution, depending on the pH. They have a positive charge in a strongly acidic medium and a negative charge in an alkaline medium. In the neutral pH range, on the other hand, they are zwitterionic. Non-ionic surfactants typically have polyether chains and do not form ions in an aqueous medium.

A. Anionic Surfactants

Anionic surfactants that can advantageously be used are acylamino acids (and their salts) such as:
- acylglutamates, for example sodium acylglutamate, di-TEA palmitoylaspartate and sodium caprylic/capric glutamate,
- acylpeptides, for example palmitoyl-hydrolysed milk protein, sodium cocoyl-hydrolysed soya protein and sodium/potassium cocoyl-hydrolysed collagen,
- sarcosinates, for example myristoyl sarcosine, TEA lauroylsarcosinate, sodium lauroylsarcosinate and sodium cocoylsarcosinate,
- taurates, for example sodium lauroyltaurate and sodium methylcocoyltaurate,
- acyllactylates, lauroyllactylate, caproyllactylate, stearoyllactylate,
- alaninates, carboxylic acids and derivatives, such as:
- lauric acid, aluminium stearate, magnesium alkanolate and zinc undecylenate,
  - carboxylic acid esters, for example calcium stearoyllactylate, laureth-6 citrate and sodium PEG-4 lauramidecarboxylate,
  - carboxylic acid ethers, for example sodium laureth-13 carboxylate and sodium PEG-6 cocamidecarboxylate,
  - phosphoric acid esters and salts, such as DEA oleth-10 phosphate and dilaureth-4 phosphate, sulfonic acids and salts, such as:
- acylisethionates, e.g. sodium/ammonium cocoylisethionate,
- alkylarylsulfonates,
- alkylsulfonates, for example sodium cocomonoglyceridesulfate, sodium $C_{12-14}$-olefinsulfonate, sodium laurylsulfoacetate and magnesium PEG-3 cocamidesulfate,
- sulfosuccinates, for example sodium dioctylsulfosuccinate, disodium laureth sulfosuccinate, disodium laurylsulfosuccinate and disodium undecylenamido MEA sulfosuccinate,
and
sulfuric acid esters such as:
- alkyl ether sulfate, for example sodium, ammonium, magnesium, MIPA and TIPA laureth sulfate, sodium myreth sulfate and sodium C12-13 pareth sulfate,
- alkylsulfates, for example sodium, ammonium and TEA laurylsulfate.

B. Cationic Surfactants

The following cationic surfactants can advantageously be used:
- alkylamines,
- alkylimidazoles,
- ethoxylated amines and
- quaternary surfactants:

$$RNH_2CH_2CH_2COO^- (at\ pH=7)$$

$$RNHCH_2CH_2COO^-B^+ (at\ pH=12), B^+ = any\ cation, e.g.\ Na^+$$

esterquats

Quaternary surfactants contain at least one N atom covalently bonded to 4 alkyl or aryl groups. This results in a positive charge, independently of the pH. Alkylbetaine, alkylamidopropylbetaine and alkylamidopropylhydroxysulfaine are advantageous. The cationic surfactants used can also preferably be selected from the group comprising quaternary ammonium compounds, especially benzyltrialkylammonium chlorides or bromides, for example benzyldimethylstearylammonium chloride, alkyltrialkylammonium salts, for example cetyltrimethylammonium chloride or bromide, alkyldimethylhydroxyethylammonium chlorides or bromides, dialkyldimethylammonium chlorides or bromides, alkylamidoethyltrimethylammonium ether sulfates, alkylpyrimidinium salts, for example laurylpyrimidinium or cetylpyridinium chloride, imidazoline derivatives, and compounds of cationic character, such as amine oxides, for example alkyldimethylamine oxides or alkylaminoethyldimethylamine oxides. Cetyltrimethylammonium salts can be used to particular advantage.

C. Amphoteric Surfactants

The following amphoteric surfactants can advantageously be used:
- acyl/dialkylethylenediamine, for example sodium acylamphoacetate, disodium acylamphodipropionate, disodium alkylamphodiacetate, sodium acylamphohydroxypropylsulfonate, disodium acylamphodiacetate and sodium acylamphopropionate,
- N-alkylamino acids, for example aminopropylalkylglutamide, alkylaminopropionic acid, sodium alkylimidodipropionate and lauroamphocarboxyglycinate.

D. Non-Ionic Surfactants

The following non-ionic surfactants can advantageously be used:
- alcohols,
- alkanolamides such as cocamides MEA/DEA/MIPA,
- amine oxides such as cocamidopropylamine oxide,
- esters formed by the esterification of carboxylic acids with ethylene oxide, glycerol, sorbitan or other alcohols,
- ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers, and alkylpolyglycosides such as laurylglucoside, decylglycoside and cocoglycoside,
- sucrose esters and ethers,
- polyglycerol esters, diglycerol esters and monoglycerol esters,
- methylglucose esters, hydroxy acid esters.

It is also advantageous to use a combination of anionic and/or amphoteric surfactants with one or more non-ionic surfactants.

The surface-active substance can be present in a concentration of between 1 and 98 wt. % in the mixtures to be used according to the invention, based on the total weight of the mixture.

A lipid phase in formulations used in the skin model according to the invention can advantageously be selected from the following groups of substances:
- mineral oils (advantageously paraffin oil), mineral waxes, fatty oils, fats, waxes and other natural and synthetic fatty substances, preferably esters of fatty acids with alcohols of low C number, e.g. with isopropanol, propylene glycol or glycerol, or esters of fatty alcohols with alkanoic acids of low C number or with fatty acids,
- alkyl benzoates,
- silicone oils such as dimethylpolysiloxanes, diethylpolysiloxanes, diphenylpolysiloxanes and mixed forms thereof,
- hydrocarbons (advantageously squalane or squalene),
- synthetic or semisynthetic triglyceride oils (e.g. triglycerides of capric or caprylic acid),
- natural oils (one or more nurturing animal and/or vegetable fats and oils, such as olive oil, sunflower oil, refined soya oil, palm oil, sesame oil, rapeseed oil, almond oil, borage oil, evening primrose oil, coconut oil, shea butter, jojoba oil, oat oil, sperm oil, tallow, neatsfoot oil and lard), and optionally other nurturing constituents, for example fatty alcohols having 8-30 C atoms, it being possible for the latter to be saturated or unsaturated and linear or branched. Examples of fatty alcohols which can be used are decanol, decenol, octanol, octenol, dodecanol, dodecenol, octadienol, decadienol, dodecadienol, oleyl alcohol, ricinoleyl alcohol (9-cis-octadecene-1,12-diol), erucyl alcohol, stearyl alcohol, isostearyl alcohol, cetyl alcohol, lauryl alcohol, myristyl alcohol, arachidyl alcohol, caprylic alcohol, capric alcohol, linoleyl alcohol, linolenyl alcohol and behenyl alcohol, and their Guerbet alcohols, the list being extendable almost without limit by other alcohols of chemically related structure. The fatty alcohols preferably originate from natural fatty acids and are conventionally prepared from the corresponding fatty acid esters by reduction. It is also possible to use fatty alcohol fractions formed by reduction from naturally occurring fats and fatty oils, e.g. tallow, groundnut oil, colza oil, cottonseed oil, soya oil, sunflower oil, palm kernel oil, linseed oil, maize oil, castor oil, rapeseed oil, sesame oil, cacao butter and coconut fat. Synthetic ester oils may also be present. Preferred esters are those of saturated and/or unsaturated, linear and/or branched alkanecarboxylic acids having 3 to 30 C atoms with saturated and/or unsaturated, linear and/or branched alcohols having 3 to 30 C atoms, and esters of aromatic carboxylic acids with saturated and/or unsaturated, linear and/or branched alcohols having 3 to 30 C atoms, selected especially from the group comprising isopropyl myristate, isopropyl stearate, isopropyl palmitate, isopropyl oleate, n-butyl stearate, n-hexyl laurate, n-decyl laurate, isooctyl stearate, isononyl stearate, isononyl isononanoate, 2-ethylhexyl palmitate, 2-ethylhexyl laurate, 2-ethylhexyl ethylhexanoate, cetearyl 2-ethylhexanoate, 3,5,5-trimethylhexyl 3,5,5-trimethylhexanoate, 2-ethylhexyl isononanoate, 2-ethylhexyl 3,5,5-trimethylhexanoate, 2-ethylhexyl 2-ethylhexanoate, 2-hexyldecyl stearate, 2-octyldecyl palmitate, oleyl oleate, oleyl erucate, erucyl oleate, erucyl erucate and synthetic or natural mixtures of such esters), fats, waxes and other natural and synthetic fatty substances, preferably esters of fatty acids with alcohols of low C number (e.g. with isopropanol, propylene glycol or glycerol) or esters of fatty alcohols with alkanoic acids of low C number or with fatty acids, alkyl benzoates (e.g. mixtures of n-dodecyl, n-tridecyl, n-tetradecyl and n-pentadecyl benzoate) and cyclic or linear silicone oils (e.g. dimethylpolysiloxanes, diethyl polysiloxanes, diphenylpolysiloxanes and mixed forms thereof).

Nurturing substances which are outstandingly suitable as or for combination with the formulations used according to the invention also include the following:
- waxes, e.g. candelilla wax or carnauba wax,
- ceramides, these being understood as meaning N-acylsphingosines (fatty acid amides of sphingosine) or synthetic analogues of such lipids (so-called pseudo-ceramides), which markedly improve the water retention capacity of the stratum corneum,
- phospholipids, for example soya lecithin, egg lecithin and kephalins,
- petrolatum and paraffin and silicone oils, the latter including, inter alia, dialkylsiloxanes and alkylarylsiloxanes, such as dimethylpolysiloxane and methylphenylpolysiloxane, and their alkoxylated and quaternized derivatives.

An aqueous phase of a formulation to be used in the skin model according to the invention can advantageously be or comprise alcohols, diols or polyols of low C number, and their ethers, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and alcohols of low C number, e.g. ethanol, isopropanol, 1,2-propanediol and glycerol, and especially one or more thickeners which can advantageously be selected from the group comprising silicon dioxide, aluminium silicates, polysaccharides or derivatives thereof, e.g. hyaluronic acid, xanthan gum and hydroxypropyl methyl cellulose, and particularly advantageously from the group comprising polyacrylates, preferably a polyacrylate from the group comprising so-called carbopols, e.g. carbopols of types 980, 981, 1382, 2984 and 5984, each individually or in combination.

Mixtures to be used according to the invention that are in the form of an emulsion advantageously comprise one or more emulsifiers. O/W emulsifiers can advantageously be selected e.g. from the group comprising polyethoxylated, polypropoxylated or polyethoxylated and polypropoxylated products, for example:
- fatty alcohol ethoxylates,
- ethoxylated wool wax alcohols,
- polyethylene glycol ethers of the general formula $$R-O-(-CH_2-CH_2-O-)_n-R',$$

- fatty acid ethoxylates of the general formula $$R-COO-(-CH_2-CH_2-O-)_n-H,$$

- etherified fatty acid ethoxylates of the general formula $$R-COO-(-CH_2-CH_2-O-)_n-R',$$

- esterified fatty acid ethoxylates of the general formula $$R-COO-(-CH_2-CH_2-O-)_n-C(O)-R',$$

- polyethylene glycol glycerol fatty acid esters,
- ethoxylated sorbitan esters,
- cholesterol ethoxylates,
- ethoxylated triglycerides,
- alkyl ether carboxylic acids of the general formula $$R-COO-(-CH_2-CH_2-O-)_n-OOH,$$

n being a number from 5 to 30,
polyethoxylated sorbitol fatty acid esters,
alkyl ether sulfates of the general formula R—O—(—CH$_2$—CH$_2$—O—)$_n$—SO$_3$—H, fatty alcohol propoxylates of the general formula R—O—(—CH$_2$—CH(CH$_3$)—O—)$_n$—H, polypropylene glycol ethers of the general formula R—O—(—CH$_2$—CH(CH$_3$)—O—)$_n$—R', propoxylated wool wax alcohols,
etherified fatty acid propoxylates R—COO—(—CH$_2$—CH(CH$_3$)—O—)$_n$—R', esterified fatty acid propoxylates of the general formula R—COO—(—CH$_2$—CH(CH$_3$)—O—)$_n$—C(O)—R', fatty acid propoxylates of the general formula R—COO—(—CH$_2$—CH(CH$_3$)—O—)$_n$—H, polypropylene glycol glycerol fatty acid esters,
propoxylated sorbitan esters,
cholesterol propoxylates,
propoxylated triglycerides,
alkyl ether carboxylic acids of the general formula R—O—(—CH$_2$—CH(CH$_3$)—O—)$_n$—CH$_2$—COOH, alkyl ether sulfates or the corresponding acids of the general formula R—O—(—CH$_2$—CH(CH$_3$)—O—)$_n$—SO$_3$—H, fatty alcohol ethoxylates/propoxylates of the general formula R—O—X$_n$—Y$_m$—H, polypropylene glycol ethers of the general formula R—O—X$_n$—Y$_m$—R', etherified fatty acid propoxylates of the general formula R—COO—X$_n$—Y$_m$—R', fatty acid ethoxylates/propoxylates of the general formula R—COO—X$_n$—Y$_m$—H.

According to the invention, the polyethoxylated, polypropoxylated or polyethoxylated and polypropoxylated O/W emulsifiers used are particularly advantageously selected from the group of substances with HLB values of 11-18, and very particularly advantageously from those with HLB values of 14.5-15.5, if they contain saturated radicals R and R'. If the O/W emulsifiers contain unsaturated radicals R and/or R', or if isoalkyl derivatives are present, the preferred HLB value of such emulsifiers can also be lower or higher.

The fatty alcohol ethoxylates are advantageously selected from the group comprising ethoxylated stearyl alcohols, cetyl alcohols and cetylstearyl alcohols (cetearyl alcohols). The Following are Particularly Preferred:
polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

The fatty acid ethoxylates can also advantageously be selected from the following group:
polyethylene glycol (20) stearate, polyethylene glycol (21) stearate, polyethylene glycol-(22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

Sodium laureth-11 carboxylate can advantageously be used as an ethoxylated alkyl ether carboxylic acid or a salt thereof. Sodium laureth-1-4 sulfate can advantageously be used as an alkyl ether sulfate. Polyethylene glycol (30) cholesteryl ether can advantageously be used as an ethoxylated cholesterol derivative. Polyethylene glycol (25) soya sterol has also proved valuable.

Polyethylene glycol (60) evening primrose glycerides can advantageously be used as ethoxylated triglycerides.

It is also advantageous to select the polyethylene glycol glycerol fatty acid esters from the group comprising polyethylene glycol (20) glyceryllaurate, polyethylene glycol (21) glyceryllaurate, polyethylene glycol (22) glyceryllaurate, polyethylene glycol (23) glyceryllaurate, polyethylene glycol (6) glycerylcaprylate/caprate, polyethylene glycol (20) glyceryloleate, polyethylene glycol (20) glycerylisostearate and polyethylene glycol (18) glyceryloleate/cocoate.

It is likewise favourable to select the sorbitan esters from the group comprising polyethylene glycol (20) sorbitan monolaurate, polyethylene glycol (20) sorbitan monostearate, polyethylene glycol (20) sorbitan mono isostearate, polyethylene glycol (20) sorbitan monopalmitate and polyethylene glycol (20) sorbitan monooleate.

The following can be used as advantageous W/O emulsifiers: fatty alcohols having 8 to 30 carbon atoms, monoglyceryl esters of saturated and/or unsaturated, branched and/or unbranched alkanecarboxylic acids with a chain length of 8 to 24 C atoms, especially 12 to 18 C atoms, diglyceryl esters of saturated and/or unsaturated, branched and/or unbranched alkanecarboxylic acids with a chain length of 8 to 24 C atoms, especially 12 to 18 C atoms, monoglyceryl ethers of saturated and/or unsaturated, branched and/or unbranched alcohols with a chain length of 8 to 24 C atoms, especially 12 to 18 C atoms, diglyceryl ethers of saturated and/or unsaturated, branched and/or unbranched alcohols with a chain length of 8 to 24 C atoms, especially 12 to 18 C atoms, propylene glycol esters of saturated and/or unsaturated, branched and/or unbranched alkanecarboxylic acids with a chain length of 8 to 24 C atoms, especially 12 to 18 C atoms, and sorbitan esters of saturated and/or unsaturated, branched and/or unbranched alkanecarboxylic acids with a chain length of 8 to 24 C atoms, especially 12 to 18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprate and glyceryl monocaprylate.

Mixtures to be used according to the invention (e.g. a topical cosmetic formulation) advantageously contain cooling agents. The following may be mentioned as examples of cooling agents: l-menthol, d-menthol, racemic menthol, menthone glyceryl acetal, menthyl lactate, substituted menthyl-3-carboxamides (e.g. menthyl-3-carboxylic acid N-ethylamide), 2-isopropyl-N-2,3-trimethylbutanamide, substituted cyclohexanecarboxamides, 3-menthoxypropane-1,2-diol, 2-hydroxyethyl menthyl carbonate, 2-hydroxypropyl menthyl carbonate, N-acetylglycine menthyl ester, isopulegol, hydroxycarboxylic acid menthyl esters (e.g. menthyl 3-hydroxybutyrate), monomenthyl succinate, 2-mercaptocyclodecanone, menthyl 2-pyrrolidin-5-onecarboxylate, 2,3-dihydroxy-p-menthane, 3,3,5-trimethylcyclohexanone glyceryl ketal, 3-menthyl-3,6-dioxaalkanoates and -trioxaalkanoates, 3-menthyl methoxyacetate and icilin.

The formulations used according to the invention (e.g. topical cosmetic formulations) also advantageously contain antimicrobial substances. Other active substances worthy of particular mention in addition to conventional preservatives, i.e. in addition to the large group of conventional antibiotics, are the products relevant to cosmetics, such as triclosan, climbazole, zinc pyrithione, ichthyol, octopirox (2-aminoethanol salt of 1-hydroxy-4-methyl-6-(2,4,4-trimethylpentyl)-2(1H)-pyridone), chitosan, farnesol, octyloxyglycerol, glyceryl monolaurate, arylalkyl alcohols, e.g. phenylethyl alcohol, 3-phenyl-1-propanol, veticol or muguet alcohol, and aliphatic diols, e.g. 1,2-decanediol, or combinations of said substances which are used, inter alia, to combat armpit odour, foot odour or scaling.

Aryl-substituted or aryloxy-substituted, unbranched or monoalkyl- or polyalkyl-branched, saturated or unsaturated
  fatty alcohols, aldehydes, acids and acid esters,
  alkanediols, dialdehydes, dicarboxylic acids and dicarboxylic acid esters
with chain lengths of $C_2$ to $C_{40}$ from a synthetic or natural source (e.g. from coconut fat, palm kernel fat, wool wax, lanolin).

Monohydroxy and oligohydroxy fatty acids with chain lengths of $C_2$ to $C_{24}$ (e.g. lactic acid, 2-hydroxypalmitic acid), their oligomers and/or polymers and vegetable and animal raw materials containing these.

Ethoxylated, propoxylated or mixed ethoxylated/propoxylated cosmetic fatty alcohols, fatty acids and fatty acid esters with chain lengths of $C_2$ to $C_{40}$ and having 1 to 150 EO and/or PO units.

It is also possible to use so-called "natural" antibacterial substances, most of which are ethereal oils. Examples of typical antibacterially active oils are those of anise, lemon, orange, rosemary, wintergreen, clove, thyme, lavender, hops, citronella, wheat, lemongrass, cedarwood, cinnamon, geranium, sandalwood, violet, eucalyptus, peppermint, gum benzoin, basil and fennel, as well as *Ocmea origanum, Hydastis carradensis, Berberidaceae daceae, Ratanhiae* or *Curcuma longa*.

Examples of important antimicrobially active substances which can be found in ethereal oils are anethole, catechol, camphene, carvacrol, eugenol, eucalyptol, ferulic acid, farnesol, hinokitiol, tropolone, limonene, menthol, methyl salicylate, thymol, terpineol, verbenone, berberin, curcumin, caryophyllene oxide, nerolidol and geraniol.

It is also possible to use mixtures of said active systems or active substances, as well as active substance combinations containing these active substances.

The amount of active substances in the preparations is preferably 0.01 to 20 wt. % and particularly preferably 0.05-10 wt. %, based on the total weight of the preparations.

Furthermore, a mixture to be used according to the invention can also be combined with sweat-inhibiting substances (antiperspirants) and odour absorbers. The antiperspirants used are primarily aluminium salts such as aluminium chloride, aluminium chlorohydrate, nitrate, sulfate, acetate, etc., and also aluminium hydroxychlorides. In addition to these, however, it can also be advantageous to use zinc, magnesium and zirconium compounds. The following can also be used: a) protein-precipitating substances such as, inter alia, formaldehyde, glutaraldehyde, natural and synthetic tannins and trichloroacetic acid, which bring about a surface occlusion of the sweat glands, b) local anaesthetics (inter alia, dilute solutions of e.g. lidocaine, prilocaine or mixtures of such substances), which switch off the sympathetic supply to the sweat glands by blocking the peripheral nerve paths, c) zeolites of the X, A or Y type, which, in addition to reducing sweat secretion, also act as adsorbents of bad odours, and d) botulinum toxin (toxin of the bacterium *Chlostridium botulinum*), and other substances that block the release of the transmitter substance acetylcholine relevant to sweat secretion.

Examples of odour absorbers are the sheet silicates described in Offenlegungsschrift DE-P 40 09 347, especially montmorillonite, kaolinite, nontronite, saponite, hectorite, bentonite and smectite, and also e.g. zinc salts of ricinoleic acid. They also include deodorants, bactericidal or bacteriostatic deodorizing substances, e.g. hexachlorophene, 2,4,4'- trichloro-2'-hydroxydiphenyl ether (Irgasan), 1,6-di(4-chlorophenylbiguanido)hexane (chlorhexidine), 3,4,4'-trichlorocarbanilide, and the active agents described in Offenlegungsschriften DE-37 40 186, DE-39 38 140, DE-42 04 321, DE-42 29 707, DE-42 29 737, DE-42 37 081, DE-43 09 372 and DE-43 24 219, which contain cationic substances, e.g. quaternary ammonium salts, and odour absorbers, e.g. ®Grillocin (combination of zinc ricinoleate and various additives) or triethyl citrate, optionally in combination with ion exchange resins.

The amount of deodorizing and/or antiperspirant substances in the mixtures is preferably 0.01 to 20 wt. % and particularly preferably 0.05-10 wt. %, based on the total weight of the preparations.

In numerous cases, the mixtures to be used in the formulations, according to the invention, can also advantageously be combined with preservatives. It is preferable here to choose preservatives like benzoic acid and its esters and salts, propionic acid and its salts, salicylic acid and its salts, 2,4-hexadienoic acid (sorbic acid) and its salts, formaldehyde and paraformaldehyde, 2-hydroxydiphenyl ether and its salts, zinc 2-sulfidopyridine N-oxide, inorganic sulfites and bisulfites, sodium iodate, chlorobutanolum, 4-ethylmercury(II)-5-amino-1,3-bis(2-hydroxybenzoic acid) and its salts and esters, dehydroacetic acid, formic acid, 1,6-bis(4-amidino-2-bromophenoxy)-n-hexane and its salts, the sodium salt of ethylmercury(II)-thiosalicylic acid, phenylmercury and its salts, 10-undecylenic acid and its salts, 5-amino-1,3-bis(2-ethylhexyl)-5-methylhexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)urea, 4-chloro-m-cresol, 2,4,4'-trichloro-2'-hydroxydiphenyl ether, 4-chloro-3,5-dimethylphenol, 1,1'-methylenebis(3-(1-hydroxymethyl-2,4-dioximidazolidin-5-yl)urea), poly(hexamethylenediguanide)hydrochloride, 2-phenoxyethanol, hexamethylenetetramine, 1-(3-chloroallyl)-3,5,7-triaza-1-azoniaadamantane chloride, 1-(4-chlorophenoxy)-1-(1H-imidazol-1-yl)-3,3-dimethyl-2-butanone, 1,3-bis(hydroxymethyl)-5,5-dimethyl-2,4-imidazolidinedione, benzyl alcohol, octopirox, 1,2-dibromo-2,4-dicyanobutane, 2,2'-methylenebis(6-bromo-4-chlorophenol), bromochlorophene, mixture of 5-chloro-2-methyl-3(2H)-isothiazolinone and 2-methyl-3(2H)-isothiazolinone with magnesium chloride and magnesium nitrate, 2-benzyl-4-chlorophenol, 2-chloroacetamide, chlorhexidine, chlorhexidine acetate, chlorhexidine gluconate, chlorhexidine hydrochloride, 1-phenoxypropan-2-ol, N-alkyl($C_{12}$-$C_{22}$)-trimethylammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxymethylurea, 1,6-bis(4-amidinophenoxy)-n-hexane and its salts, glutaraldehyde, 5-ethyl-1-aza-3,7-dioxabicyclo(3.3.0)octane, 3-(4-chlorophenoxy)-1,2-propanediol, hyamines, alkyl($C_8$-$C_{18}$)dimethylbenzylammonium chloride, alkyl($C_8$-$C_{18}$)dimethylbenzylammonium bromide, alkyl($C_8$-$C_{18}$)dimethylbenzylammonium saccharinate, benzyl hemiformal, 3-iodo-2-propynylbutyl carbamate or sodium hydroxymethylaminoacetate.

Formulations used in the skin model according to the invention, especially dermatological formulations, can also advantageously contain dyestuffs and/or coloured pigments, especially if they are to be used in the decorative cosmetics sector. The dyestuffs and coloured pigments can be selected from the appropriate positive list of the cosmetics regulations or from the EC list of cosmetic colourants. In most cases they are identical to the dyestuffs permitted for foods. Examples of advantageous coloured pigments are titanium dioxide, mica, iron oxides (e.g. $Fe_2O_3$, $Fe_3O_4$, FeO(OH)) and/or tin oxide. Examples of advantageous dyestuffs are carmine, Berlin blue, chromium oxide green, ultramarine blue and/or manganese violet. Mixtures of said active systems can also be used.

SPECIFIC EMBODIMENTS

In specific embodiment one, the invention comprises use of an ex vivo human skin sample for simulating or analyzing a treatment of human or animal skin, wherein said sample comprises an epidermis, dermis and a subcutis layer, and wherein said subcutis layer has an average thickness of 0.5 to 5 mm.

In specific embodiment two, the invention comprises use according to specific embodiment one, wherein the subcutis layer comprises a hair follicle.

In specific embodiment three, the invention comprises a method of modelling, simulating or analyzing a selected effect of a selected treatment of human or animal skin, comprising the steps of:
a) Providing a skin sample of a human, the sample including an epidermis, dermis and a subcutis layer, said subcutis layer having an average thickness of 0.5 to 5 mm,
b) subjecting the sample to the selected treatment, and
c) observing the effect of the treatment on the skin sample.

In specific embodiment four, the invention comprises the method of specific embodiment three, wherein the skin sample comprises at least one primary hair follicle and preferably has a hair follicle density of at least two follicles per $cm^2$.

In specific embodiment five, the invention comprises the method of any of specific embodiments three to four, wherein the skin sample is a skin sample of abdomen, thigh or breast, preferably a skin sample of abdomen.

In specific embodiment six, the invention comprises the method of any of specific embodiments three to five, wherein the skin sample is a skin sample of a female human.

In specific embodiment seven, the invention comprises the method of any of specific embodiments three to six, wherein the skin sample comprises a subcutis layer with an average thickness of at least 1 mm.

In specific embodiment eight, the invention comprises the method of any of specific embodiments three to seven, wherein the skin sample has a dimension (length×width×thickness) of (5-10)×(5-10)×(2-5) mm.

In specific embodiment nine, the invention comprises the method of any of specific embodiments three to eight, wherein the effects to be observed are
a) effects of exposition of the skin sample to substances, the substances being applied topically to the skin sample and/or systemically to the skin sample by mixing with a culture medium, and/or
b) effects of skin sample irradiation.

In specific embodiment ten, the invention comprises the method of any of specific embodiments three to nine for the assessment of:
modulation of skin and/or hair pigmentation,
modulation of hair growth,
modulation of skin and/or hair viability and/or proliferation,
modulation of fat metabolism,
anti-cellulite properties of substances,
slimming,
anti-aging effects, particularly by fat cell stimulation
allergenic potential and/or irritation,
UV protection, particularly UV erythema prevention, alleviation and healing,
effects induced by visible light or infra red light
effects caused by mechanical stress as e.g. abrasion or pressure modulation of connecting tissue properties, particularly for the assessment of anti-wrinkle properties of substances,
anti-oxidative effects,
wound healing,
modulation of skin barrier function,
modulation of ion channels, especially neurofunctional channels and preferably channels activated by GABA, glutamate, acetylcholine, serotonin, adrenalin and ATP, and temperature sensitive channels (TRPM8, TRPV3, TRPV4, TRPV1, ANKTM/TRPA1, TRPV2),
immunestimulation, immunesuppression,
sebum stimulation, sebum suppression,
anti-microbial effectiveness, particularly anti-acne effectiveness,
sweat secretion decrease,
substantivity of materials on a skin surface,
film forming effectiveness,
modulation of skin and hair thickness,
moisturization,
phototoxicity,
skin metabolism
penetration properties
release properties from formulations
of compounds.
In specific embodiment eleven, the invention comprises a system for modelling a selected effect of a selected treatment of human skin, comprising an isolated skin sample of a human being, the sample including an epidermis, dermis and a subcutis layer, and wherein the subcutis layer has an average thickness of 0.5 to 5 mm.
In specific embodiment twelve, the invention comprises the system according to specific embodiment eleven, wherein the skin sample is a skin sample of abdomen, thigh or breast, preferably from a female human.
In specific embodiment thirteen, the invention comprises the system according to any of specific embodiments eleven or twelve, wherein the skin sample is placed with its subcutis layer on a support comprising a cultivation medium.

It is claimed:

1. An in vitro method for modeling, simulating or analyzing one or more selected effect(s) of a selected treatment for human or animal skin, comprising:
    a) providing a human skin sample having a hair follicle density of 2-14 hair follicles per $cm^2$ that is viable for at least 8 days comprising an epidermis, dermis, and subcutis layer, said subcutis layer having an average thickness of 0.5 to 5 mm,
    b) subjecting the sample to the selected treatment, and
    c) observing the effect(s) of the treatment on the skin sample.

2. The method of claim 1, wherein the skin sample is a skin sample of abdomen, thigh or breast.

3. The method of claim 1, wherein the skin sample is a skin sample of a female human.

4. The method of claim 1, wherein the skin sample comprises a subcutis layer with an average thickness of 1 to 3 mm.

5. The method of claim 1, wherein the skin sample has a dimension (length×width×thickness) of (5-10)×(5-10)×(2-5) mm.

6. The method of claim 1, wherein the effects to be observed are
    a) effects of exposition of the skin sample to substances, the substances being applied topically to the skin sample and/or systemically to the skin sample by mixing with a culture medium, and/or
    b) effects of skin sample irradiation.

7. The method of claim 1, further comprising (d) the assessment of the human skin sample for:
    modulation of skin and/or hair pigmentation,
    modulation of hair growth,
    modulation of skin and/or hair viability and/or proliferation,
    modulation of fat metabolism,
    anti-cellulite properties of substances,
    slimming,
    anti-aging effects, particularly by fat cell stimulation,
    allergenic potential and/or irritation,
    UV protection, particularly UV erythema prevention, alleviation and healing,
    effects induced by visible light or infra red light,
    effects caused by mechanical stress as e.g. abrasion or pressure,
    modulation of connecting tissue properties, particularly for the assessment of anti-wrinkle properties of substances,
    anti-oxidative effects,
    wound healing,
    modulation of skin barrier function,
    modulation of ion channels,
    immunostimulation, immunosuppression,
    sebum stimulation, sebum suppression,
    anti-microbial effectiveness, particularly anti-acne effectiveness,
    sweat secretion decrease,
    substantivity of materials on a skin surface,
    film forming effectiveness,
    modulation of skin and hair thickness,
    moisturization,
    phototoxicity,
    skin metabolism,
    penetration properties, and/or
    release properties from formulations of compounds.

8. The method of claim 2, wherein the skin sample is a skin sample of abdomen.

9. The method of claim 7, wherein the ion channels are neurofunctional channels selected from the group consisting of: channels activated by GABA, glutamate, acetylcholine, serotonin, adrenalin or ATP, and temperature sensitive channels such as TRPM8, TRPV3, TRPV4, TRPV1, ANKTM/TRPA1, or TRPV2.

10. The method of claim 1, wherein the skin sample is viable for at least 12 days.

11. The method of claim 1, wherein the skin sample is viable for at least 18 days.

12. The method of claim 1, wherein the skin sample has a hair follicle density of 2-10 hair follicles per $cm^2$.

13. The method of claim 1, wherein the skin sample is taken from a human wherein blood circulation has not stopped for more than 10 minutes.

14. The method of claim 1, wherein the skin sample is taken from a human 18-60 years of age.

15. The method of claim 2, wherein the skin sample is a skin sample of thigh.

16. The method of claim 5, wherein the skin sample has a dimension (length×width×thickness) of (8-10)×(8-10)×(3-4) mm.

* * * * *